United States Patent [19]
Ha

[11] Patent Number: 6,106,458
[45] Date of Patent: Aug. 22, 2000

[54] ANESTHETIC LARYNGOSCOPE WITH MANUAL CONTROLLED OXYGEN EJECTION MEANS

[76] Inventor: Da Ha, No. 5 Unit 1, Building 147, Hospital 253, Aiminlu, Huhehaote City, Neimenggu 010062, China

[21] Appl. No.: 09/180,174

[22] PCT Filed: May 5, 1997

[86] PCT No.: PCT/CN97/00040

§ 371 Date: Nov. 4, 1998

§ 102(e) Date: Nov. 4, 1998

[87] PCT Pub. No.: WO97/41768

PCT Pub. Date: Nov. 13, 1997

[30] Foreign Application Priority Data

May 6, 1996 [CN] China .................................. 96106088

[51] Int. Cl.⁷ .................................................. A61B 1/267
[52] U.S. Cl. ........................................... 600/187; 600/185
[58] Field of Search .................................. 600/120, 131, 600/185, 187, 190, 193, 194, 196, 197, 199, 237

[56] References Cited

U.S. PATENT DOCUMENTS

| | | | |
|---|---|---|---|
| 2,854,004 | 9/1958 | Durrant | 604/264 |
| 3,826,248 | 7/1974 | Gobels | 600/193 |
| 3,941,120 | 3/1976 | Lee . | |
| 4,126,127 | 11/1978 | May . | |
| 4,384,570 | 5/1983 | Roberts | 600/187 |
| 4,681,094 | 7/1987 | Rolnick . | |
| 4,947,896 | 8/1990 | Bartlett | 600/187 |
| 5,394,865 | 3/1995 | Salerno | 600/199 |
| 5,551,946 | 9/1996 | Bullard | 600/194 |

FOREIGN PATENT DOCUMENTS

| | | |
|---|---|---|
| 88203809 U | 11/1988 | China . |
| 2046364 | 10/1989 | China . |
| 2094963 U | 2/1992 | China . |
| 2100183 U | 4/1992 | China . |
| 1101220A | 7/1984 | Russian Federation . |

*Primary Examiner*—Michael Peffley
*Assistant Examiner*—Brad C. Blaise
*Attorney, Agent, or Firm*—Finnegan, Henderson, Farabow, Garrett & Dunner, L.L.P.

[57] ABSTRACT

An anesthetic laryngoscope for manual oxygen jet-ventilation, including a handle with a handle housing having a lower end, a first oxygen supply tube, and a battery container mounted in the handle housing. A blade having an observation light and a second oxygen supply tube mounted thereon is mounted on the lower end of the handle means. The first oxygen supply tube is connected to the second oxygen supply tube, and a manual oxygen on/off valve is provided on one of the first and second oxygen supply tubes. Preferably, the manual oxygen on/off valve is a manually controlled two-position, two-way valve to enable generation of a pulsing supply of oxygen through an ejector nozzle at the end of the second oxygen supply tube.

5 Claims, 5 Drawing Sheets

A − A

ANESTHETIC LARYNGOSCOPE WITH MANUAL CONTROLLED OXYGEN EJECTION MEANS

BACKGROUND OF THE INVENTION

1. Field of the Invention

The present invention in general relates to a laryngoscope used as a medical instrument, and in particular, to an anesthetic laryngoscope with manual oxygen jet-ventilation means.

2. Description of the Related Art

It is well known in the art that a laryngoscope is used to expose a patient's glottis for tracheal intubation during cardiopulmonary resuscitation or induction of general anesthesia. Currently, the commonly used methods for opening the patient's airway during cardiopulmonary resuscitation are described as below.

Mouth-to-mouth artificial respiration is advantageous because of its immediate availability. However, this method may induce to exhaustion of the operator's physical strength during the operation and its effect is not reliable. In addition, this method has a possibility of spreading some diseases between the patient and the medical staff.

Esophagus obturator airway is convenient to use and is easily available. However, some potential complications such as apnea or gastric distention could be caused due to accidentally entering into the patient's trachea during the process. Therefore, esophagus rupture is likely to happen when the tube is drawn out without deflating the cuff. As for the patient whose respiratory reflex has not been restored, it is necessary or desirable to perform tracheal intubation to prevent regurgitation when the esophagus obturator airway is pulled out. The most serious disadvantage is that the face mask is very difficult to attach properly to the patient's face with the result that hyperventilation and hypercapnia may occur.

Tracheal intubation may be administered to maintain the airway unobstructed so that aspiration and stomach distention will not occur. After that, under an intermittent positive pressure ventilation may be carried out. Also, endotracheal suction can be performed directly. Therefore, tracheal intubation can be considered as a very reliable method for keeping the respiratory airway clear throughout the cardiopulmonary resuscitation.

However, tracheal intubation has some technical difficulties in use and takes a certain time (preferably not more than 15–20 seconds) to administer. At the same time, successful administration is subject to the influence of physical factors of the patient, such as an obese body, a short neck or a high laryngeal protuberance. Sometimes, although the larynx has been exposed, the glottis can not be seen clearly, thereby it is difficult to insert the tube. If the period of non-ventilation lasts too long, the tissue anoxia tends to be more serious. Thus, the patient's situation will be aggravated and the operation may end with unexpected failure.

In order to decrease death risk and increase the survival rate in such cases, the inventor has disclosed a multifunctional laryngoscope in his prior Chinese Patent No. 88203809.5, the disclosure of which is incorporated herein by reference.

That patent discloses an improvement on the conventional laryngoscope, in which a tank for storing drugs and a tube for supplying a jet of oxygen are provided. The purpose of the improvement is to provide a laryngoscope which can supply not only a stream of oxygen but also administer atomizing anesthesia in glottis during a tracheal intubation procedure. However, a drawback of that kind of laryngoscope is that it can not produce pulses during intubation in the cardiopulmonary resuscitation process so that jet ventilation can not be achieved.

If necessary, an open-type special jet respirator should be used in combination. The mechanism of this respirator switches the gas flow on and off by opening and closing an electromagnetic valve of the respirator to generate pulses of oxygen flow. An oxygen supply tube provided on the laryngoscope blade ejects a supply of oxygen flow in front of the exposing glottis so that streams of oxygen can enter into lungs and make hemithorax elevation until gas exchange can be achieved.

Since this open-type special ejection respirator is powered by storage batteries during field emergency treatment, it is bulky, heavy and expensive. In addition, it is not easy to carry while moving from one place to another. These drawbacks have virtually limited the scope of use of the laryngoscope in field emergency treatment. Although the open-type special ejection respirator is provided with manual oxygen blocking valve means to prevent the electromagnetic valve from being ineffective, it is necessary to involve an assistant to handle said valve means. Therefore, it is not convenient to use during the intubation procedure.

SUMMARY OF THE INVENTION

In order to overcome the above-mentioned disadvantages of the prior art laryngoscopes, an object of the invention is to provide an anesthetic laryngoscope having manual oxygen jet-ventilation means, which is not restricted by the place of use and can be used to rescue patients without delay. The laryngoscope of the invention is small in volume and convenient to use. In addition, it is easy to be produced with lower cost.

To accomplish the object of the invention, there is provided an anesthetic laryngoscope with manual oxygen jet-ventilation means, comprising: handle means having a handle housing, a first oxygen supply tube and a battery container mounted in the housing; blade means provided at the lower end of the handle means and having an observation light and a second oxygen supply tube. The anesthetic laryngoscope is characterized in that the first oxygen supply tube is connected to the second oxygen supply tube, and either one of the first and second oxygen supply tubes is provided with a manual oxygen on/off valve.

In a preferable embodiment of the invention, the manual oxygen on/off valve is a manually controlled two position-two way valve and is preferably positioned on the laryngoscope handle.

In an exemplary embodiment in accordance with this invention, the diameter of the second oxygen supply tube is in the range of about 1 mm. to 2 mm, preferably 1.63 mm. The distance between the ejector nozzle for oxygen and the top of the laryngoscope blade ranges from 1 mm to 2.5 cm.

Moreover, the ejector nozzle for oxygen is slightly converged, and its diameter is in the range of about 0.6 mm to 0.8 mm.

These and the other features and advantages of the present invention will become apparent to those skilled in the art upon reading the following detailed description when being taken in conjunction with the drawings wherein there are shown and described some illustrative embodiments of the invention, which do not mean to limit the protection scope of the invention.

BRIEF DESCRIPTION OF THE DRAWINGS

In the following detailed description, reference will be made to the attached drawings in which.

DETAILED DESCRIPTION OF THE PREFERRED EMBODIMENTS

Figure 1:
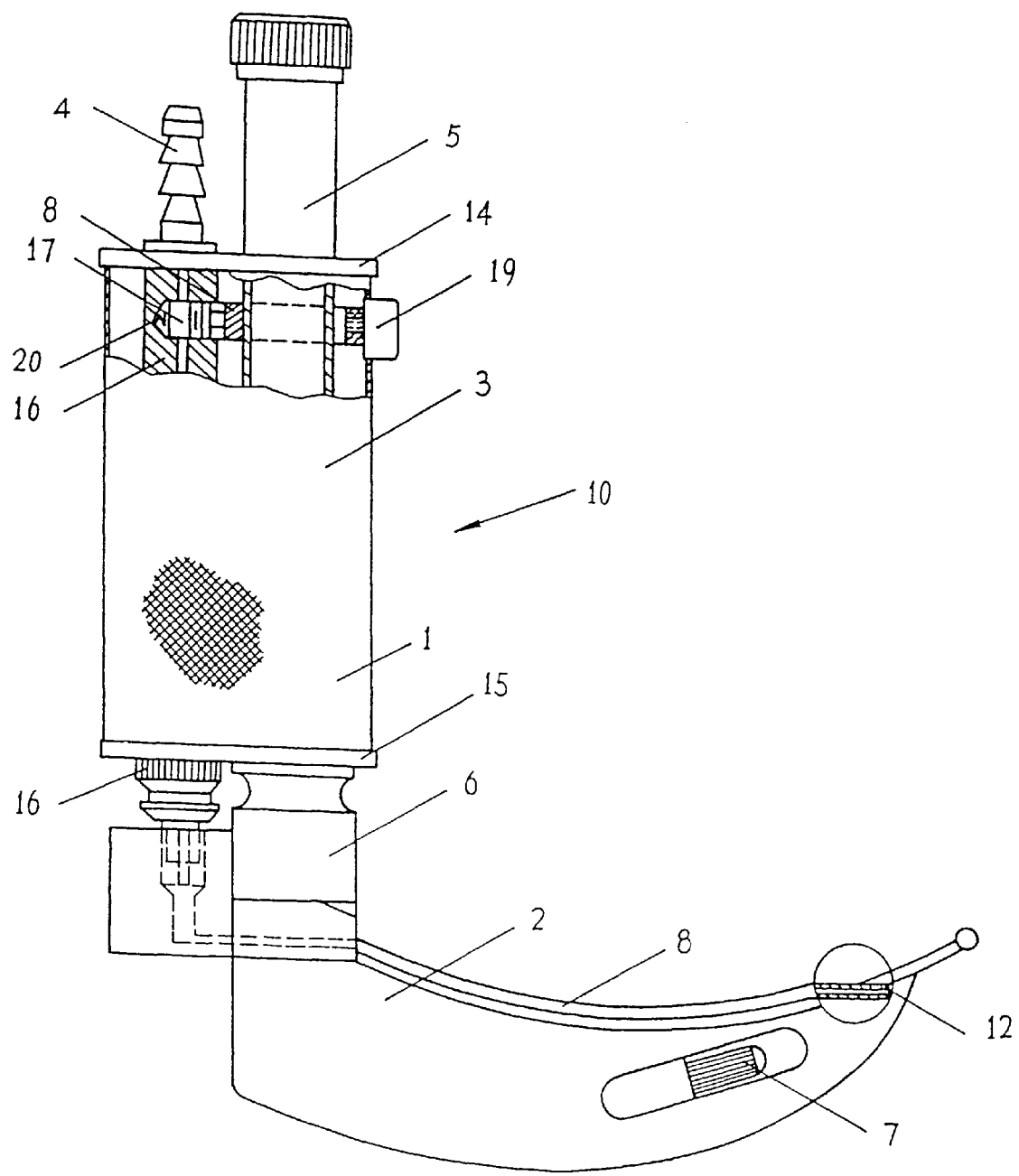
FIG. 1 is a partially cross sectional view of the anesthetic laryngoscope with manual oxygen jet-ventilation means according to one preferable embodiment of the invention.
Figure 2:
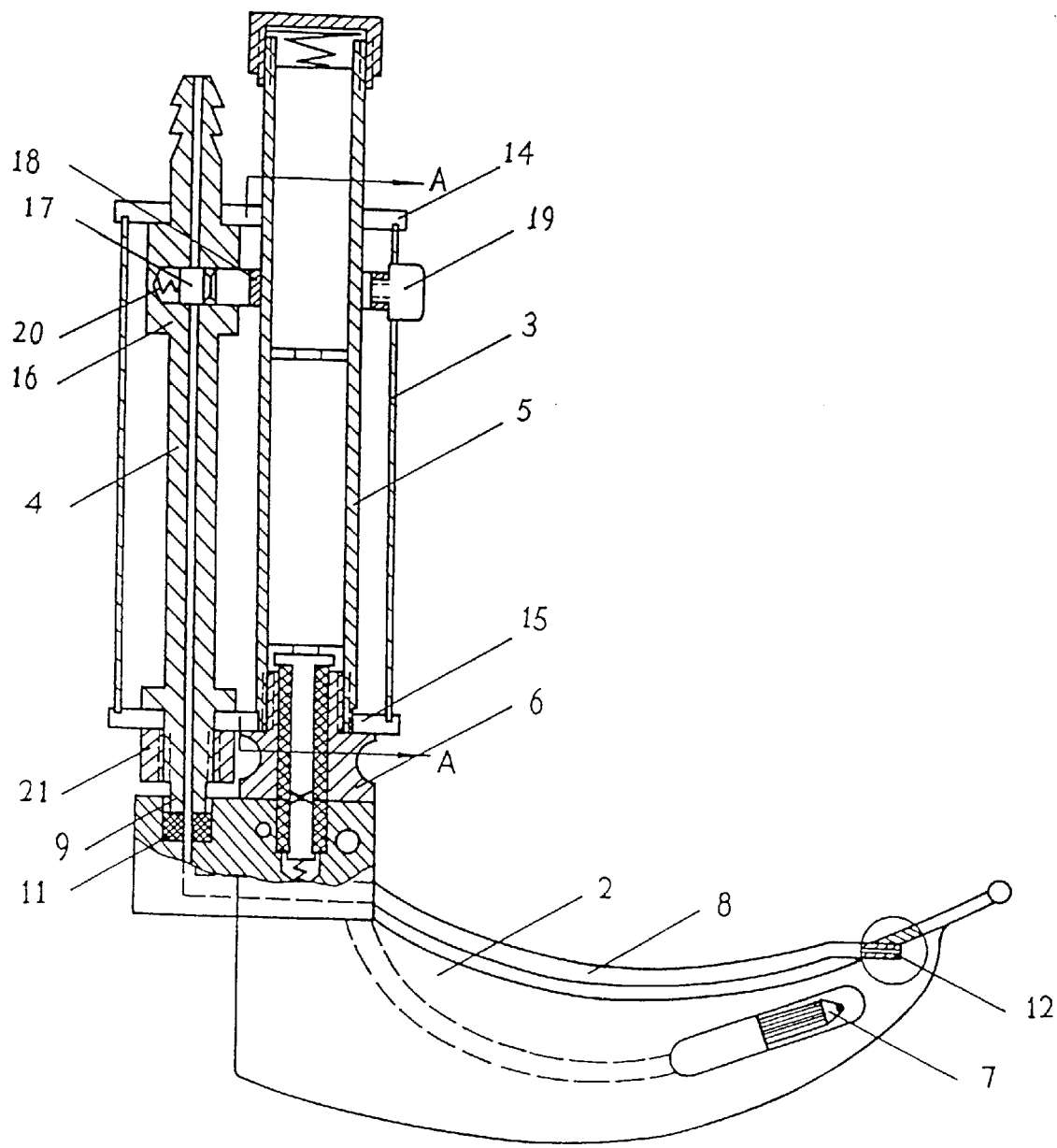
FIG. 2 is a sectional view of the anesthetic laryngoscope with manual oxygen jet-ventilation means according to one preferable embodiment of the invention.
Figure 3:
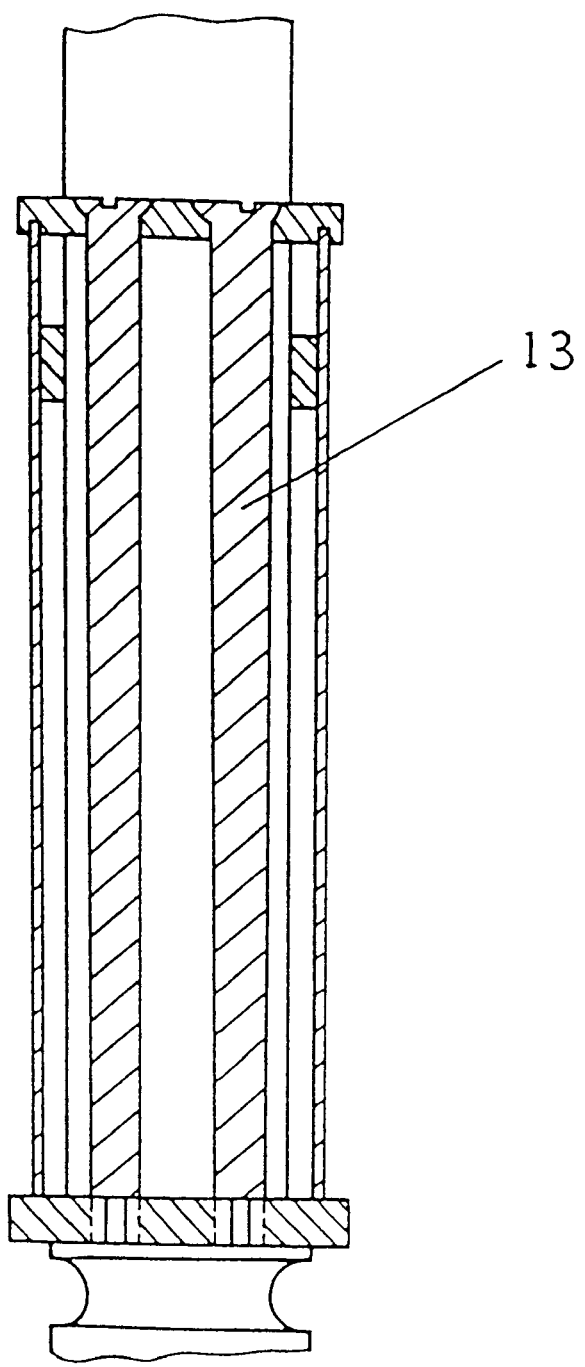
FIG. 3 is a sectional view taken along the line A—A in FIG. 2.

As shown in FIGS. 1 to 3, a laryngoscope, generally designated by the reference numeral 10, includes a laryngoscope handle 1 and a laryngoscope blade 2 for insertion into the patient's mouth. The laryngoscope handle 1 has a handle housing 3 in which an oxygen supply tube 4 and a battery container 5 are mounted therein.

Moreover, the handle housing 3 is retained securely between a top cover 14 and a bottom cover 15. A screw stem 13 is also secured between the top cover 14 and the bottom cover 15. A length of thread is provided on the rear end of the oxygen supply tube 4, and a nut 21 is threaded thereon to fix the top cover 14 and the bottom cover 15 together.

The laryngoscope blade 2 is attached at the bottom end of the laryngoscope handle 1 and is engaged in a socket 6 provided on the bottom end of the laryngoscope handle 1. An observation light 7 and an oxygen supply tube 8 are provided on the laryngoscope blade 2, respectively.

A recess 9 is formed on the rear end of the laryngoscope blade 2, in which a gasket 11 is provided therein so that the oxygen supply tube 8 of the laryngoscope blades 2 can be fitted and communicated with an ejector nozzle for oxygen provided on the bottom end of the oxygen supply tube 4.

It should be understood that the shape and the size of the laryngoscope blade 2 will be varied depending on the patient's age. Therefore, the engagement of the oxygen supply tubes 4 and 8 will facilitate interchangeability of different laryngoscope blades 2.

The ejector nozzle 12 for oxygen of the oxygen supply tube 8 is situated on the laryngoscope blade 2 at a distance 1–2.5 cm from the tip end thereof. The diameter of the oxygen supply tube 8 is about 1–2 mm, preferably 1.63 mm. The ejector nozzle for oxygen 12 is slight converged and its diameter is about 0.6–0.8 mm.

The laryngoscope handle 1 is provided with a manual oxygen on/off valve which comprises a valve body 16, a valve core 17 and a valve rod 18. The valve body 16 is mounted on the oxygen supply tube 4. The valve rod 18 is connected with a control knob 19 and bypasses the battery container 5 to control the valve core 17. A return spring 20 is provided at the end of the valve core 17.

The manual oxygen on/off valve can be provided in any position along the oxygen supply tubes. From a practical standpoint, however, it is preferable that this manual oxygen on/off valve is provided on the laryngoscope handle so that it is convenient to be handled.

Figure 4:
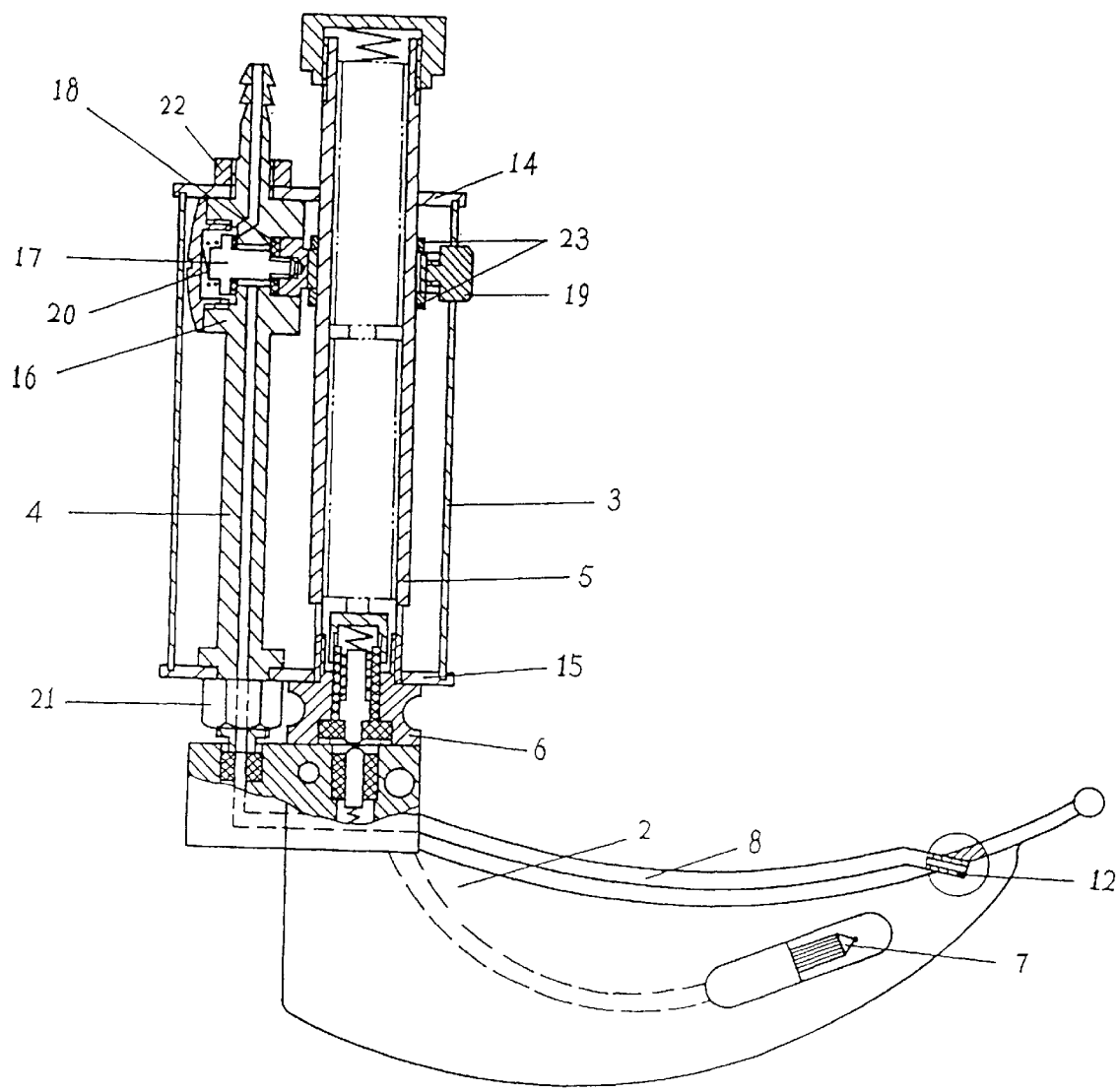
FIG. 4 is a sectional view of the anesthetic laryngoscope with manual oxygen jet-ventilation means according to another preferred embodiment of the invention.

In FIG. 4, another preferred embodiment of the anesthetic laryngoscope with manual oxygen jet-ventilation means according to the invention is shown, wherein the corresponding components are designated by the same reference numerals as those of the above-described embodiment, respectively.

Figure 5:
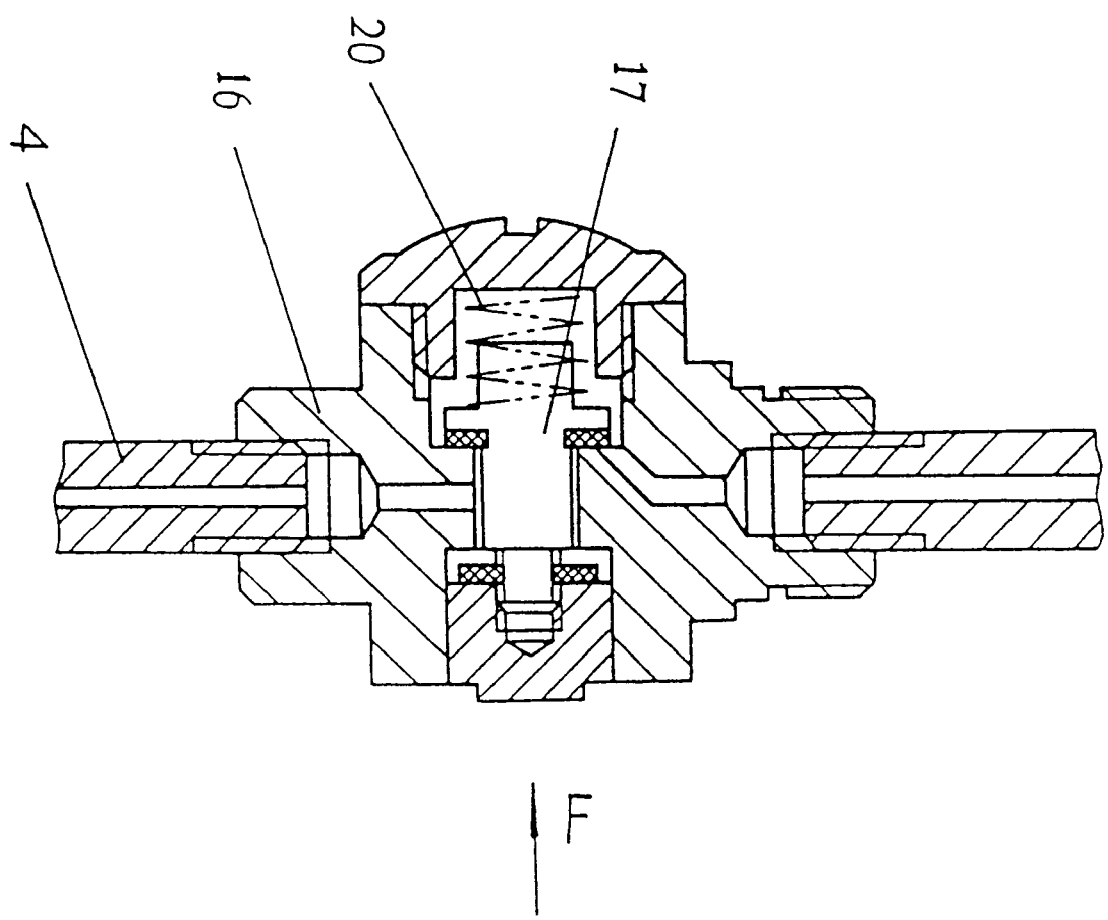
FIG. 5 is a detail of the oxygen on/off valve provided in the anesthetic laryngoscope shown in FIG. 4.

The difference between the embodiments shown in FIGS. 1–3 and FIG. 4 respectively is that a different kind of two-position and two-way oxygen valve is mounted on the laryngoscope as shown in FIG. 4. This kind of two-position and two-way oxygen valve is shown in detail in FIG. 5 and has a better seal effect.

In addition, the connection of the handle housing 3 to the top cover 14 and the bottom cover 15 is modified. More specifically, upper and lower nuts 21, 22 provided on the oxygen supply tube 4 are used to mount the handle housing 3 securely between the top cover 14 and the bottom cover 15. The advantage of this arrangement is that the valve rod of the oxygen valve is easier to move.

As shown in FIG. 4, on the outer wall of the battery container, a guide means 23 for positioning the oxygen valve in the transverse direction is provided in the form of an upper and lower flanges so that a more properly directional action of the valve rod will be facilitated.

It will be understood to those skilled in the art that other types of valves can be adopted to control the supply of oxygen through the oxygen supply tube, and that the connection of the handle housing 3 to the top cover and the bottom cover can be modified.

The laryngoscope according to the invention can be used in combination with a small and adjustable pressure oxygen bottle. Thus, the laryngoscope of the invention is portable and can be carried with various appendages, such as simplified respirator, manually operated aspirator, endotracheal tube, bit-block, etc.

In the course of providing patient care, particularly in an emergency situation, an operator firstly connects the laryngoscope according to the invention to an oxygen supply source and adjusts the oxygen pressure, that is, for adult, the pressure is set to be 0.12–0.25 MPa; for children, 0.08–0.1 MPa; for neonates, 0.04–0.06 MPa.

After that, the operator holds the laryngoscope 10 by his/her left hand and adjusts the angle formed between the laryngoscope handle 2 and the laryngoscope blade 3 to be 90°. At the same time, the electric source and the oxygen source are switched on, respectively.

After the patient's head has been placed in an optimum position, the operator opens the patient's mouth and lifts his/her lower jaw by using the thumb, fore-finger and middle finger of his/her right hand and sweep the patient's labium inferius.

When the laryngoscope is put into the patient's mouth, his/her tongue is pushed to the left side and the laryngoscope blade 2 is moved to the center of the patient's mouth. Here, the patient's uvula can be seen, which is the first mark of exposing the patient's glottis.

Then, the laryngoscope is advanced slowly until its tip end reaches the root of the patient's tongue. After the laryngoscope is lifted up slightly, the border of the patient's epiglottis can be seen, which is the second mark of exposing the patient's glottis.

At this moment, the control knob 19 provided on the laryngoscope handle of the present invention is pushed down by the fore-finger of the operator's left hand so that the pulses of the oxygen flow can be created. Thus, the operator can ventilate the patient while he is exposing the glottis.

Even when only the end of larynx has been exposed, but the glottis of the patient can not be seen clearly due to the patient obesity, short neck or high laryngeal protuberance, the gas flow can be introduced through the glottis into the trachea so as to achieve the gas exchange.

It should be understood, however, that even though the purposes and numerous characteristics of the present invention have been set forth in the foregoing description, the disclosure is illustrative only, and modifications and variations to the embodiments of the invention described above may be made by persons skilled in the art without departing from the spirit and scope of the invention defined by the appended claims.

The laryngoscope according to the invention eliminates the non-aerated phase occurred during the tracheal intubation and increases the safety, reliability of the tracheal intubation procedure and the success rate of emergency treatment.

The laryngoscope according to the invention has advantages in that it can rapidly open the airway during the operation so that the supply of oxygen can be restored in time. In addition, the manually controlled frequency of operating the oxygen on/off valve can be selected at 12–35 times/min.

In the case that regurgitation occurs in the course of the emergency, the operator may supply the patient with oxygen under unobstructed view while sucking out of food, so that sucking food out and supplying with oxygen can be carried out alternatively. The laryngoscope according to the invention is very useful, particularly for neonate resuscitation.

What is claimed is:

1. An anesthetic laryngoscope for manual oxygen jet-ventilation, comprising:

handle means including a handle housing having a lower end, a first oxygen supply tube, and a battery container mounted in said handle housing; and blade means on the lower end of said handle means and having an observation light and a second oxygen supply tube mounted thereon;

wherein said first oxygen supply tube is connected to said second oxygen supply tube, and a manual oxygen on/off valve is provided on one of said first and second oxygen supply tubes.

2. The anesthetic laryngoscope of claim 1, wherein said manual oxygen on/off valve is provided on said first oxygen supply tube.

3. The anesthetic laryngoscope of claim 1, wherein said manual oxygen on/off valve provided on one of said first and second oxygen supply tubes is a manually controlled two-position, two-way valve.

4. The anesthetic laryngoscope of claim 1, wherein said second oxygen supply tube provided on said blade means has a diameter in the range of from about 1 mm to 2 mm, and including an ejector nozzle on said second oxygen supply tube for ejecting oxygen flow, said ejector nozzle being slightly converged and positioned in a range of about 1 mm to about 2.5 cm away from a tip of said blade means, said ejector nozzle having a diameter in a range of from about 0.6 mm to 0.8 mm.

5. The anesthetic laryngoscope of claim 2, including guiding means for positioning said manual oxygen on/off valve in a transverse direction, said guiding means being provided on an outer wall of said battery container.

* * * * *